(12) United States Patent
Yoon

(10) Patent No.: US 10,357,165 B2
(45) Date of Patent: Jul. 23, 2019

(54) METHOD AND APPARATUS FOR ACQUIRING BIOINFORMATION AND APPARATUS FOR TESTING BIOINFORMATION

(71) Applicant: SAMSUNG ELECTRONICS CO., LTD., Suwon-si (KR)

(72) Inventor: Youngzoon Yoon, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/068,760

(22) Filed: Mar. 14, 2016

(65) Prior Publication Data

US 2017/0055855 A1    Mar. 2, 2017

(30) Foreign Application Priority Data

Sep. 1, 2015  (KR) .......................... 10-2015-0123658

(51) Int. Cl.
*A61B 5/021*    (2006.01)
*A61B 5/00*    (2006.01)
(Continued)

(52) U.S. Cl.
CPC ........ *A61B 5/02141* (2013.01); *A61B 5/0261* (2013.01); *A61B 5/0295* (2013.01); *A61B 5/681* (2013.01); *A61B 2562/043* (2013.01)

(58) Field of Classification Search
CPC ... A61B 5/0059; A61B 5/0062; A61B 5/0064; A61B 5/0071
(Continued)

(56) References Cited

U.S. PATENT DOCUMENTS 4,987,900 A    1/1991    Eckerle et al.
5,065,765 A    11/1991    Eckerle et al.
(Continued)

FOREIGN PATENT DOCUMENTS

CN    104257371 A    1/2015
CN    10-4970781 A    10/2015
(Continued)

OTHER PUBLICATIONS

X.F. Teng and Y.T. Zhang, "Continuous and Noninvasive Estimation of Arterial Blood Pressure Using a Photoplethysmographic Approach", Proceedings of the 25th Annual International Conference of the IEEE Engineering in Medicine and Biology Society, Cancun, Mexico, Sep. 17-21, 2003, pp. 3153-3156.
(Continued)

*Primary Examiner* — Allen Porter
(74) *Attorney, Agent, or Firm* — Sughrue Mion, PLLC

(57)    ABSTRACT

An apparatus for acquiring bioinformation, including a laser irradiator configured to irradiate a laser beam onto a region of interest including blood vessels; a sensor configured to detect a first change in a laser speckle pattern generated by the laser beam reflected from the region of interest; and a processor configured to acquire a biosignal indicating a second change in blood flow within the blood vessels based on the detected first change in the laser speckle pattern, and to acquire the bioinformation by using the biosignal, wherein the laser beam emitted from the laser irradiator is incident at an angle to the region of interest.

12 Claims, 9 Drawing Sheets

(51) Int. Cl.
*A61B 5/026* (2006.01)
*A61B 5/0295* (2006.01)

(58) Field of Classification Search
USPC .................................................. 600/479, 480
See application file for complete search history.

(56) References Cited

U.S. PATENT DOCUMENTS

| | | | |
|---|---|---|---|
| 5,265,011 A | 11/1993 | O'Rourke | |
| 5,891,022 A | 4/1999 | Pologe | |
| 6,161,038 A | 12/2000 | Schookin et al. | |
| 6,475,153 B1 | 11/2002 | Khair et al. | |
| 6,571,193 B1 | 5/2003 | Unuma et al. | |
| 7,123,363 B2 | 10/2006 | Puttappa et al. | |
| 7,231,243 B2 | 6/2007 | Tearney et al. | |
| 7,463,796 B2 | 12/2008 | Borgos et al. | |
| 7,641,614 B2 | 1/2010 | Asada et al. | |
| 7,657,135 B2 | 2/2010 | Borgos et al. | |
| 7,737,947 B2 | 6/2010 | Schroeder et al. | |
| 7,822,299 B2 | 10/2010 | Borgos et al. | |
| 7,925,056 B2 | 4/2011 | Presura et al. | |
| 8,032,200 B2 | 10/2011 | Tearney et al. | |
| 8,089,465 B2 | 1/2012 | Lutian | |
| 8,111,953 B2 | 2/2012 | Borgos et al. | |
| 8,217,897 B2 | 7/2012 | Lutian | |
| 8,277,384 B2 | 10/2012 | Fine | |
| 8,313,439 B2 | 11/2012 | McCombie et al. | |
| 8,343,062 B2 | 1/2013 | Fortin et al. | |
| 8,343,063 B2 | 1/2013 | Borgos | |
| 8,360,985 B2 | 1/2013 | Borgos | |
| 8,467,636 B2 | 6/2013 | Borgos et al. | |
| 8,496,595 B2 | 7/2013 | Jornod | |
| 8,808,188 B2 | 8/2014 | Banet et al. | |
| 8,868,149 B2 | 10/2014 | Eisen et al. | |
| 8,954,135 B2 | 2/2015 | Yuen et al. | |
| 9,097,516 B2 | 8/2015 | Hotta et al. | |
| 9,149,216 B2 | 10/2015 | Eisen et al. | |
| 9,277,868 B2 | 3/2016 | Borgos et al. | |
| 9,282,931 B2 | 3/2016 | Tearney et al. | |
| 9,326,711 B2 | 5/2016 | Kracker et al. | |
| 9,510,758 B2 | 12/2016 | Warger, II et al. | |
| 9,596,990 B2 | 3/2017 | Park et al. | |
| 9,603,524 B2 | 3/2017 | Park et al. | |
| 9,636,041 B2 | 5/2017 | Zalevsky et al. | |
| 9,668,672 B2 | 6/2017 | Zalevsky et al. | |
| 9,704,050 B2 | 7/2017 | Lee et al. | |
| 2002/0007125 A1 | 1/2002 | Hickey | |
| 2002/0095092 A1 | 7/2002 | Kondo et al. | |
| 2003/0013976 A1 | 1/2003 | Freund et al. | |
| 2004/0186387 A1 | 9/2004 | Kosuda et al. | |
| 2005/0228297 A1 | 10/2005 | Banet et al. | |
| 2007/0078308 A1* | 4/2007 | Daly | A61B 3/117 |
| | | | 600/310 |
| 2007/0163353 A1 | 7/2007 | Lec et al. | |
| 2007/0265533 A1 | 11/2007 | Tran | |
| 2007/0276262 A1 | 11/2007 | Banet et al. | |
| 2007/0276632 A1 | 11/2007 | Banet et al. | |
| 2008/0071180 A1 | 3/2008 | Borgos | |
| 2008/0146952 A1 | 6/2008 | Presura et al. | |
| 2008/0181556 A1 | 7/2008 | Borgos et al. | |
| 2008/0183053 A1 | 7/2008 | Borgos et al. | |
| 2008/0228089 A1 | 9/2008 | Cho et al. | |
| 2009/0069698 A1 | 3/2009 | Bae et al. | |
| 2009/0073461 A1 | 3/2009 | Borgos et al. | |
| 2009/0209834 A1 | 8/2009 | Fine | |
| 2009/0209871 A1 | 8/2009 | Ueki et al. | |
| 2009/0326393 A1 | 12/2009 | Sethi et al. | |
| 2010/0022861 A1 | 1/2010 | Cinbis et al. | |
| 2010/0049059 A1 | 2/2010 | Ha et al. | |
| 2010/0145171 A1 | 6/2010 | Park et al. | |
| 2010/0160798 A1 | 6/2010 | Banet et al. | |
| 2010/0168589 A1 | 7/2010 | Banet et al. | |
| 2010/0210930 A1 | 8/2010 | Saylor | |
| 2010/0210956 A1 | 8/2010 | Im | |
| 2010/0324384 A1 | 12/2010 | Moon et al. | |
| 2011/0021931 A1 | 1/2011 | Borgos et al. | |
| 2011/0172505 A1 | 7/2011 | Kim et al. | |
| 2011/0208066 A1 | 8/2011 | Gnadinger | |
| 2012/0025185 A1 | 2/2012 | Kasamatsu | |
| 2012/0108956 A1 | 5/2012 | Warger, II et al. | |
| 2012/0130215 A1 | 5/2012 | Fine et al. | |
| 2012/0130253 A1 | 5/2012 | Nadkarni et al. | |
| 2012/0130260 A1 | 5/2012 | Borgos et al. | |
| 2012/0136261 A1 | 5/2012 | Sethi et al. | |
| 2012/0143066 A1* | 6/2012 | Antonelli | A61B 5/021 |
| | | | 600/480 |
| 2012/0191001 A1 | 7/2012 | Segman | |
| 2013/0046192 A1 | 2/2013 | Lin et al. | |
| 2013/0131475 A1 | 5/2013 | Eisen et al. | |
| 2013/0144137 A1 | 6/2013 | Zalevsky et al. | |
| 2013/0190630 A1 | 7/2013 | Borgos | |
| 2013/0218025 A1 | 8/2013 | Tverskoy | |
| 2013/0245456 A1 | 9/2013 | Ferguson, Jr. et al. | |
| 2014/0012146 A1 | 1/2014 | Fukuda | |
| 2014/0066788 A1 | 3/2014 | Mukkamala et al. | |
| 2014/0066793 A1 | 3/2014 | Mukkamala et al. | |
| 2014/0081153 A1 | 3/2014 | Kuno | |
| 2014/0107493 A1 | 4/2014 | Yuen et al. | |
| 2014/0125491 A1 | 5/2014 | Park et al. | |
| 2014/0127996 A1 | 5/2014 | Park et al. | |
| 2014/0148658 A1 | 5/2014 | Zalevsky et al. | |
| 2014/0200423 A1 | 7/2014 | Eisen et al. | |
| 2014/0288435 A1* | 9/2014 | Richards | A61B 5/02427 |
| | | | 600/479 |
| 2015/0105638 A1 | 4/2015 | Eisen et al. | |
| 2015/0117015 A1 | 4/2015 | Roh et al. | |
| 2015/0119725 A1 | 4/2015 | Martin et al. | |
| 2015/0126820 A1 | 5/2015 | Muhlsteff | |
| 2015/0323311 A1 | 11/2015 | Muijs et al. | |
| 2016/0058300 A1* | 3/2016 | Yoon | A61B 5/0059 |
| | | | 600/480 |
| 2016/0066790 A1 | 3/2016 | Shcherbakov et al. | |
| 2016/0103985 A1 | 4/2016 | Shim et al. | |
| 2016/0106325 A1 | 4/2016 | Kang et al. | |
| 2016/0106327 A1* | 4/2016 | Yoon | A61B 5/02108 |
| | | | 600/480 |
| 2016/0106333 A1 | 4/2016 | Kang et al. | |
| 2016/0113589 A1 | 4/2016 | Yoon | |
| 2016/0157736 A1 | 6/2016 | Huang et al. | |
| 2016/0192845 A1 | 7/2016 | Warger et al. | |
| 2016/0198961 A1 | 7/2016 | Homyk et al. | |
| 2016/0206251 A1 | 7/2016 | Kwon et al. | |
| 2016/0256116 A1 | 9/2016 | Baik et al. | |
| 2016/0256117 A1 | 9/2016 | Baik et al. | |
| 2016/0278645 A1* | 9/2016 | Yoon | A61B 5/02141 |
| 2016/0278718 A1 | 9/2016 | Fujii et al. | |
| 2016/0287109 A1 | 10/2016 | Shim et al. | |
| 2016/0357154 A1 | 12/2016 | Shim et al. | |
| 2017/0017858 A1 | 1/2017 | Roh et al. | |
| 2017/0049340 A1 | 2/2017 | Cho et al. | |
| 2017/0065184 A1 | 3/2017 | Barak | |
| 2017/0105679 A1 | 4/2017 | Gil | |
| 2017/0112395 A1 | 4/2017 | Kim et al. | |
| 2017/0135636 A1 | 5/2017 | Park et al. | |
| 2017/0150930 A1 | 6/2017 | Shikii et al. | |
| 2017/0172510 A1 | 6/2017 | Homyk et al. | |
| 2017/0209047 A1 | 7/2017 | Zalevsky et al. | |
| 2017/0245796 A1 | 8/2017 | Zalevsky et al. | |
| 2017/0251926 A1 | 9/2017 | Yooon et al. | |
| 2017/0319146 A1 | 11/2017 | Park et al. | |

FOREIGN PATENT DOCUMENTS

| | | |
|---|---|---|
| DE | 10 2010 014 761 A1 | 10/2011 |
| EP | 0755221 B1 | 10/2001 |
| EP | 1 204 370 B1 | 4/2008 |
| EP | 3072441 A1 | 9/2016 |
| JP | 11-155826 A | 6/1999 |
| JP | 2000-166885 A | 6/2000 |
| JP | 2003-532478 A | 11/2003 |
| JP | 3769524 B2 | 4/2006 |
| JP | 2008-295576 A | 12/2008 |
| JP | 4506849 B2 | 7/2010 |

(56) References Cited

FOREIGN PATENT DOCUMENTS

| | | |
|---|---|---|
| JP | 4614184 B2 | 1/2011 |
| JP | 4645259 B2 | 3/2011 |
| JP | 4848732 B2 | 12/2011 |
| JP | 2012-57962 A | 3/2012 |
| JP | 2012-161507 A | 8/2012 |
| JP | 2012-187300 A | 10/2012 |
| JP | 2012202776 A | 10/2012 |
| JP | 2013509225 A | 3/2013 |
| JP | 2014-23031 A | 2/2014 |
| JP | 5528816 B2 | 6/2014 |
| JP | 2014240782 A | 12/2014 |
| JP | 2015502197 A | 1/2015 |
| KR | 10-0610813 B1 | 8/2006 |
| KR | 10-0650044 B1 | 11/2006 |
| KR | 10-2008-0073988 A | 8/2008 |
| KR | 10-2009-0052442 A | 5/2009 |
| KR | 10-2010-0060141 A | 6/2010 |
| KR | 10-2010-0065084 A | 6/2010 |
| KR | 10-1007354 B1 | 1/2011 |
| KR | 1020110025100 A | 3/2011 |
| KR | 10-1040598 B1 | 6/2011 |
| KR | 10-1058152 B1 | 8/2011 |
| KR | 10-1065615 B1 | 9/2011 |
| KR | 10-2012-0057813 A | 6/2012 |
| KR | 10-1310464 B1 | 9/2013 |
| KR | 10-2014-0024845 A | 3/2014 |
| KR | 101503604 B1 | 3/2015 |
| KR | 10-1560287 B1 | 10/2015 |
| KR | 10-1564066 B1 | 10/2015 |
| KR | 10-2016-0041553 A | 4/2016 |
| KR | 10-2016-0088127 A | 7/2016 |
| KR | 10-2016-0107007 A | 9/2016 |
| KR | 10-2016-0108081 A | 9/2016 |
| KR | 10-2017-0104361 A | 9/2017 |
| KR | 10-2017-0124943 A | 11/2017 |
| WO | 2015/129949 A1 | 9/2015 |

OTHER PUBLICATIONS

Y.S. Yan and Y.T. Zhang, "Noninvasive Estimation of Blood Pressure Using Photoplethysmographic Signals in the Period Domain", Proceedings of the 2005 IEEE Engineering in Medicine and Biology 27th Annual Conference, Shanghai, China, Sep. 1-4, 2005, pp. 3583-3584.

Zhang et al., "A LabVIEW Based Measure System for Pulse Wave Transit Time"; Proceedings of the 5th International Conference on Information Technology and Application in Biomedicine, in conjunction with the 2nd International Symposium & Summer School on Biomedical and Health Engineering; May 30-31, 2008; 4 pgs. Total, pp. 477-480.

Fortino et al., "PPG-based Methods for Non Invasive and Continuous Blood Pressure Measurement: an Overview and Development Issues in Body Sensor Networks"; IEEE; 2010; 4 pgs. total.

Kurylyak, et al., "A Neural Network-based Method for Continuous Blood Pressure Estimation from a PPG Signal"; Instrumentation and Measurement Technology Conference (I2MTC); May 6-9, 2013; 4pgs. Total, pp. 280-283.

Young-Zoon Yoon.,"Study on cardiovascular system with blood pressure waveform and heart rate variability", A Dissertation Submitted to the Faculty of Seoul National University in Partial Fulfillment of the Requirements for the Degree of Doctor of Philosophy, School of Physics, Graduate School, Seoul National University, 2005, (210 Pages Total).

Chen et al., "Estimation of Central Aortic Pressure Waveform by Mathematical Transformation of Radial Tonometry Pressure; Validation of Generalized Transfer Function", 1997: 95, 1827-36, 12 pages total, American Heart Association.

O'Rourke et al., "Pulse wave analysis", Research Methods in Human Cardiovascular Pharmacology, 2001, Clinical Pharmacology, Blackwell Science Ltd Br J Clin Pharmacol: 51, pp. 507-522, 16 pages total.

Aymen A. Awad et al., "How Does the Plethysmogram Derived from the Pulse Oximeter Relate to Arterial Blood Pressure in Coronary Artery Bypass Graft Patients?"; Anesth Analg, 93; 2001; pp. 1466-1471; 6 pgs. total.

Satomi Suzuki, et al., "Cuffless and Non-invasive Systolic Blood Pressure Estimation for Aged Class by Using a Photoplethysmograph"; 30th Annual International IEEE EMBS Conference; Aug. 20-24, 2008; pp. 1327-1330; 4 pgs. total.

Arata Suzuki et al., "Feature Selection Method for Estimating Systolic Blood Pressure Using the Taguchi Method"; IEEE Transactions on Industrial Informatics; vol. 10; No. 2; May 2014; pp. 1077-1085; 9 pgs. total.

Y. Kurylyak et al., "Photoplethysmogram-based Blood Pressure Evaluation using Kalman Filtering and Neural Networks"; Medical Measurements and Applications Proceedings (MeMeA), 2013 IEEE International Symposium; May 4, 2013; 5 pgs. total.

Yevgeny Beiderman et al., "Remote estimation of blood pulse pressure via temporal tracking of reflected secondary speckles pattern"; Journal of Biomedical Optics; vol. 15; No. 6; Nov./Dec. 2010; pp. 061707-1-061707-7; 7 pgs. total.

Yu.N. Kul'chin et al., "Correlation method for processing speckles of signals from single-fibre multimode interferometers by using charge-coupled devices"; Optical Fibres and Waveguides; Quantum Electronics; vol. 36; No. 4; 2006; pp. 339-342; 5 pgs. total.

Enric Monte-Moreno., "Non-invasive estimate of blood glucose and blood pressure from a photoplethysmograph by means of machine learning techniques", Artificial Intelligence in Medicine, vol. 53, 2011, pp. 127-138, 12 Pages total.

Communication dated Aug. 30, 2016 issued by the European Patent Office in counterpart European Patent Application No. 16158751.4.

Ramakrishna Mukkamala et al., "Towards Ubiquitous Blood Pressure Monitoring via Pulse Transit Time: Theory and Practice", IEEE Trans Biomed Eng. Aug. 2015 ; 62(8), pp. 1879-1901, 48 pages total.

Qing Liu et al., "Attenuation of Systolic Blood Pressure and Pulse Transit Time Hysteresis During Exercise and Recovery in Cardiovascular Patients", IEEE Transactions on Biomedical Engineering, vol. 61, No. 2, Feb. 2014, pp. 346-352.

R. A. Payne et al., "Pulse transit time measured from the ECG: an unreliable marker of beat-to-beat blood pressure", J Appl Physiol, the American Physiological Society 100, 2006, pp. 136-141.

Communication from United States Patent and Trademark Office dated Jun. 28, 2017, in U.S. Appl. No. 14/844,437.

Communication from United States Patent and Trademark Office dated Mar. 20, 2017, in U.S. Appl. No. 14/818,420.

Communication from United States Patent and Trademark Office dated Jun. 16, 2017, in U.S. Appl. No. 14/818,420.

Jianjun Qiu et al; "Spatiotemporal laser speckle contrast analysis for blood flow imaging with maximized speckle contrast"; Journal of Biomedical Optics; vol. 15; No. 1; Jan./Feb. 2010; pp. 016003-1-016003-5; 5pgs. total.

Dr. S. Shah et al; "Optoelectronic blood pressure estimation: A novel principle for blood pressure measurement"; Tarilian Laser Technologies; (http://www.tarilian-lasertechnologies.com/press/tlt-at-esh2012.php); 2012; 4 pgs. total.

"Tarilian Laser Technologies achieves greatest technological advance in blood pressure measurement for 130 years"; (http://www.tarilian-lasertechnologies.com/press/pr111201.php); Tarilian Laser Technologies; Dec. 7, 2011; 6 pgs. total.

Communication dated Dec. 14, 2017 issued by the European Patent Office in counterpart Application No. 17172684.7.

Final Office Action dated May 23, 2018 by United States Patent and Trademark Office in U.S. Appl. No. 14/862,288.

Non-Final Office Action dated May 25, 2018 by United States Patent and Trademark Office in U.S. Appl. No. 14/961,145.

Notice of Allowance dated Nov. 7, 2018, issued by United States Patent and Trademark Office in U.S. Appl. No. 14/844,437.

Notice of Allowance dated Nov. 15, 2018, issued by United States Patent and Trademark Office in U.S. Appl. No. 14/818,420.

Restriction Requirement dated Sep. 6, 2018 issued by the United States Patent and Trademark Office in U.S. Appl. No. 14/884,019.

Advisory Action dated Aug. 2, 2018 by the United States Patent and Trademark Office in U.S. Appl. No. 14/862,288.

(56) References Cited

OTHER PUBLICATIONS

Non-Final Office Action dated Jul. 26, 2018 by the United States Patent and Trademark Office in U.S. Appl. No. 14/833,221.
Non-Final Office Action dated Aug. 6, 2018 by the United States Patent and Trademark Office in U.S. Appl. No. 14/818,420.
Non-Final Office Action dated Jun. 15, 2018 by the U.S. Patent and Trademark Office in U.S. Appl. No. 14/844,437.
Final Office Action dated Feb. 28, 2018 by the United States Patent and Trademark Office in U.S. Appl. No. 14/961,145.
Final Office Action dated Mar. 8, 2018 by the United States Patent and Trademark Office in U.S. Appl. No. 14/844,437.
Restriction Requirement dated Mar. 8, 2018 by the United States Patent and Trademark Office in U.S. Appl. No. 14/833,221.
Non-Final Office Action dated Dec. 22, 2017 issued by the United States Patent and Trademark Office in U.S. Appl. No. 14/818,420.
Non-Final OA dated Aug. 24, 2017 issued by the United States Patent and Trademark Office in U.S. Appl. No. 14/844,437.
Non-Final Office Action dated Sep. 27, 2017 issued by the United States Patent and Trademark Office in U.S. Appl. No. 14/961,145.
Non-Final Office Action dated Nov. 1, 2017 issued by the United States Patent and Trademark Office in U.S. Appl. No. 14/862,288.
Restriction Requirement dated Jan. 14, 2019 issued by the United States Patent and Trademark Office in U.S. Appl. No. 15/654,422.
Non-Final Office dated Dec. 14, 2018 issued by the United States Patent and Trademark Office in U.S. Appl. No. 14/884,019.
Anonymous, ""Central Venous Pressure Waveforms"", Section 3: Anesthesia Management, Part B: Monitoring, Chapter 30: Cardiovascular Monitoring, 1979, http://web.squ.edu.om/med-Lib/MED_CD/E_CDs/anesthesia/site/content/v03/030275r0O.HTM; 4 pages total.
Office Action dated Feb. 15, 2019 issued by the U.S. Patent and Trademark Office in U.S. Appl. No. 14/961,145.
Notice of Allowance dated Mar. 4, 2019 issued by the USPTO in counterpart U.S. Appl. No. 14/318,420.
Final Office Action dated Mar. 7, 2019 issued by the USPTO in counterpart U.S. Appl. No. 14/833,221.
Non-Final Office Action dated Mar. 22, 2019 issued by the USPTO in counterpart U.S. Appl. No. 14/362,288.
Notice of Allowance dated Apr. 24, 2019, issued by the USPTO in counterpart U.S. Appl. No. 14/961,145.
Non-Final Office Action dated Apr. 26, 2019 issued by the USPTO in counterpart U.S. Appl. No. 15/654,422.

\* cited by examiner

METHOD AND APPARATUS FOR ACQUIRING BIOINFORMATION AND APPARATUS FOR TESTING BIOINFORMATION

CROSS-REFERENCE TO RELATED APPLICATION

This application claims benefit from Korean Patent Application No. 10-2015-0123658, filed on Sep. 1, 2015, in the Korean Intellectual Property Office, the disclosure of which is incorporated herein in its entirety by reference.

BACKGROUND

1. Field

The present disclosure relates to a method and apparatus for acquiring bioinformation and an apparatus for testing bioinformation, and more particularly, to a method and apparatus for acquiring bioinformation by using an optical sensor in a non-invasive manner and an apparatus, which includes the apparatus for acquiring bioinformation, for testing bioinformation.

2. Description of the Related Art

Blood pressure or blood flow information may be used to analyze a state of health of a person. In general, blood pressure is crucial biological information, including information regarding a cardiac output, elasticity of blood vessels, and a physiological change of a subject.

Blood pressure may be measured using an invasive or non-invasive method. An example of an invasive method involves directly measuring pressure of blood vessels by inserting a catheter into the blood vessels. However, this method cannot be conveniently and frequently used to check a state of health of a person due to the insertion of the catheter and a risk of bleeding in arteries.

Non-invasive methods may include auscultation, oscillometry, tonometry, and the like. Auscultation and oscillometry are performed to measure blood pressure by using a cuff. Through auscultation, systolic pressure and diastolic pressure of a subject may be measured by measuring Korotkoff sounds that are generated as the cuff gradually contracts. Also, oscillometry may be performed to measure an actual change of pressure in the cuff as the cuff contracts. Tonometry may be performed to measure a change of an internal arterial pressure by using a sensor placed on an artery in a state in which an effect of tension of blood vessel walls is removed by pressing the artery in such a manner that an external carotid artery having skeletal support such as radial artery has a planar portion. However, the above-described non-invasive methods are not appropriate to measure a blood pressure change of a person in real time.

SUMMARY

Additional aspects will be set forth in part in the description which follows and, in part, will be apparent from the description, or may be learned by practice of the presented exemplary embodiments.

According to an aspect of an exemplary embodiment, an apparatus for acquiring bioinformation includes a laser irradiator configured to irradiate a laser beam onto a region of interest including blood vessels; a sensor configured to detect a first change in a laser speckle pattern generated by the laser beam reflected from the region of interest; and a processor configured to acquire a biosignal indicating a second change in blood flow within the blood vessels based on the detected first change in the laser speckle pattern, and to acquire the bioinformation by using the biosignal, wherein the laser beam emitted from the laser irradiator is incident at an angle to the region of interest.

The laser irradiator may be arranged to be positioned at the angle with respect to the region of interest.

The apparatus may further include a first optical element configured to adjust an irradiation direction of the laser beam.

The sensor may extend in a direction with respect to the region of interest.

The sensor may further include a plurality of sensor devices, and the plurality of sensor devices may be spaced apart from each other at intervals in a direction with respect to the region of interest.

The apparatus may further include a second optical element configured to selectively adjust the irradiation direction of the laser beam by modifying a refraction index of the second optical element according to a control signal transmitted by the processor.

The apparatus may further include a displacement measurer configured to measure a change in a distance between the laser irradiator and the region of interest.

The refraction index may be determined based on the distance between the laser irradiator and the region of interest, the distance being measured by the displacement measurer.

The first optical element may further include a meta material structure.

The sensor may further include one or more sensor devices that may be spaced apart from each other at respective intervals in a direction with respect to the region of interest, and the laser irradiator may further include one or more laser irradiation devices that may be arranged respectively corresponding to the one or more sensor units.

According to another aspect of an exemplary embodiment, a bioinformation testing apparatus includes a main body; straps connected to the main body, and an apparatus for acquiring the bioinformation arranged on at least one from among an inner surface of the main body or an inner surface of the straps.

The apparatus may further include a plurality of sensors and laser irradiators, the plurality of sensors and laser irradiators being spaced apart from each other on an inner surface of the straps at intervals in a direction in which the straps extend.

When a subject wears the bioinformation testing apparatus by using the straps, the apparatus of acquiring the bioinformation may be arranged in a direction parallel to a forearm of the subject.

According to yet another aspect of an exemplary embodiment, a method of acquiring bioinformation includes irradiating a laser beam onto a region of interest including blood vessels, wherein an irradiation direction of the laser beam is adjusted; detecting a change in a laser speckle pattern from the region of interest; acquiring a biosignal indicating a change in blood flow within the blood vessels using the detected change in the laser speckle pattern; and acquiring the bioinformation by using the biosignal.

A distance between a laser irradiator and the region of interest may be measured, and the irradiation direction of the laser beam may be adjusted based on the measured distance between the laser irradiator and the region of interest.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

The terms used in this specification are those general terms currently widely used in the art in consideration of functions relating to the present disclosure, but the terms may vary according to the intention of those of ordinary skill in the art, precedents, or new technology in the art. Also, specific terms may be selected by the applicant, and in this case, the detailed meaning thereof may be described in the detailed description of the present disclosure. Thus, the terms used in the specification should be understood not as simple names but based on the meaning of the terms and the overall description of the present disclosure.

Throughout the specification, when a portion "includes" an element, another element may be further included, rather than excluding the existence of the other element, unless otherwise described. Also, throughout the specification, the terms " . . . unit", " . . . module", etc. are units for processing at least one function or operation and may be implemented as hardware, software, or a combination of hardware and software.

The present disclosure will now be described more fully with reference to the accompanying drawings, in which exemplary embodiments of the present disclosure are shown. The present disclosure may, however, be embodied in many different forms and should not be construed as being limited to the embodiments set forth herein; rather, these embodiments are provided so that this disclosure will be thorough and complete, and will fully convey the concept of the present disclosure to those of ordinary skill in the art.

Hereinafter, the present disclosure will be described in detail by explaining exemplary embodiments of the present disclosure with reference to the attached drawings.

Figure 1:
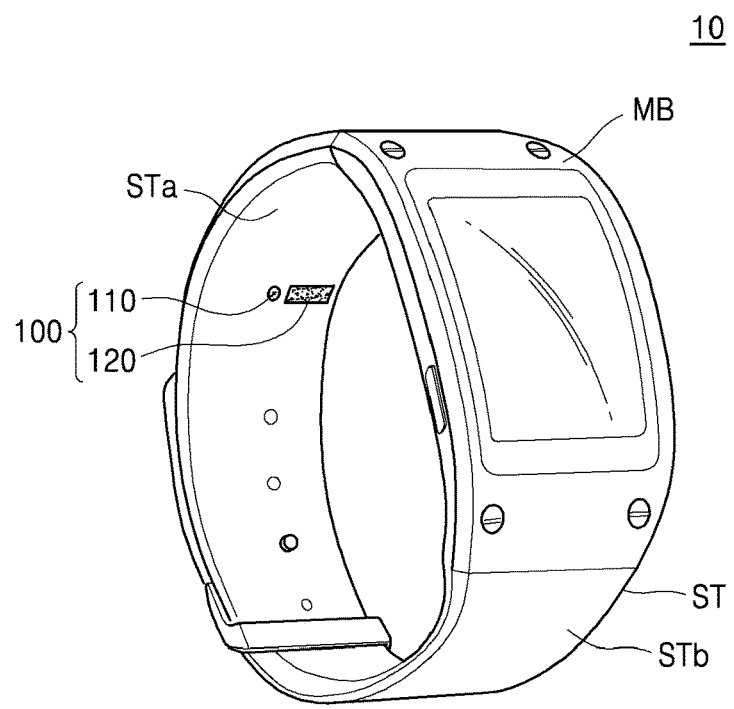
FIG. 1 illustrates a perspective view of an exterior of a bioinformation testing apparatus according to an exemplary embodiment.
Figure 2A:
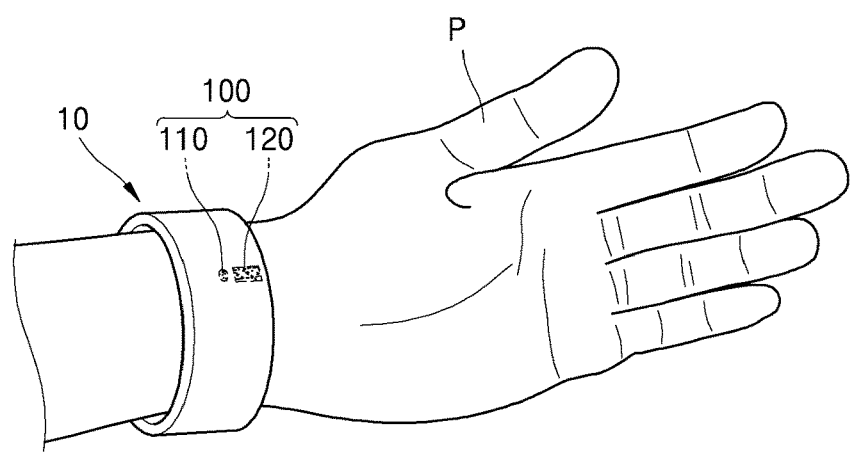
FIGS. 2A and 2B illustrates an example of a bioinformation measuring position with respect to a bioinformation testing apparatus, according to an exemplary embodiment.
Figure 2B:
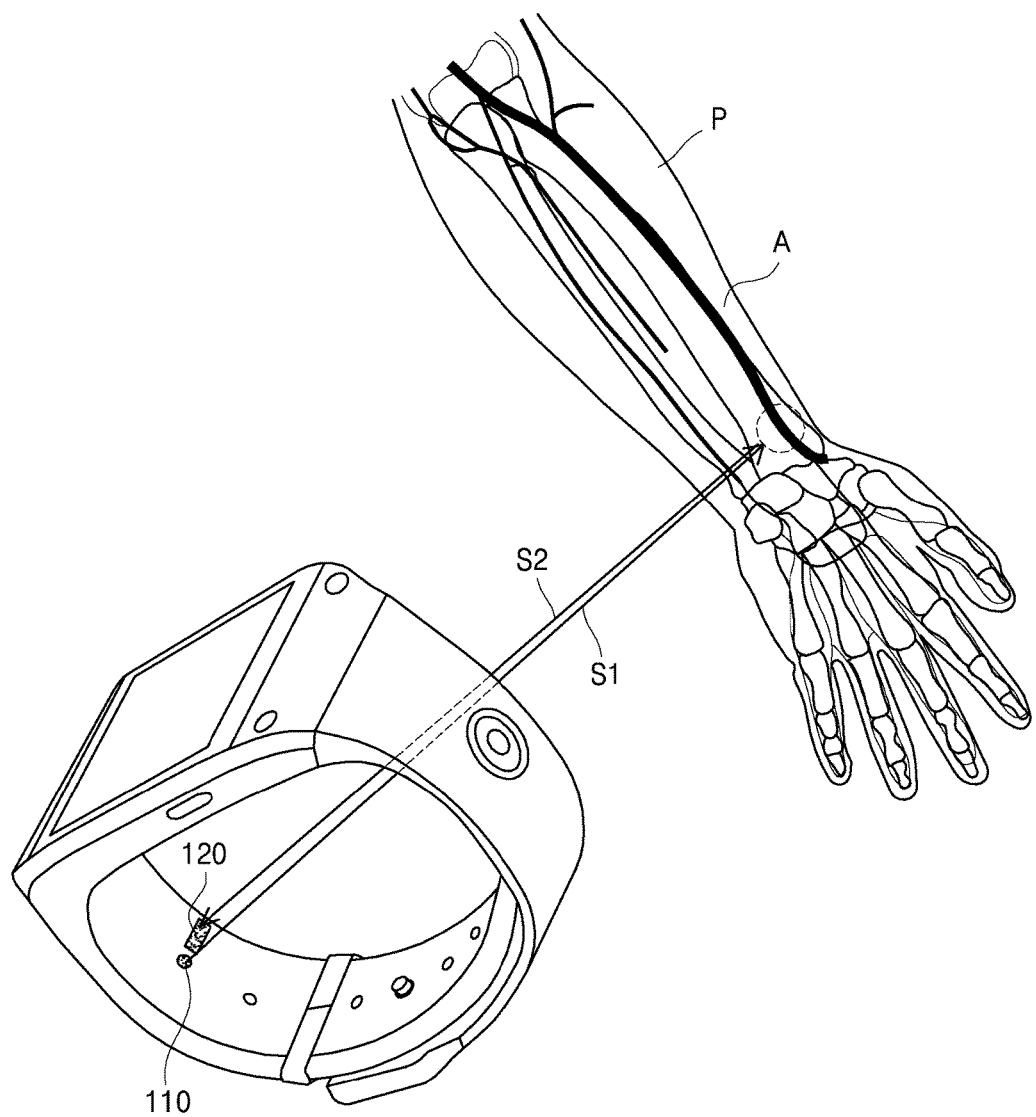

FIG. 1 illustrates a perspective view of an exterior of an example of a bioinformation testing apparatus 10 according to an exemplary embodiment. FIGS. 2A and 2B illustrates an example of a bioinformation measuring position with respect to the bioinformation testing apparatus 10, according to an exemplary embodiment.

Referring to FIGS. 1 to 2B, the bioinformation testing apparatus 10 may be a watch or a wearable device of a wrist-band type. However, the present disclosure is not limited thereto, and the bioinformation testing apparatus 10 may be a wearable device of, for example, a glasses type, a ring type, or a necklace type.

The bioinformation testing apparatus 10 may include a main body MB and straps ST, and the straps ST are connected to the main body MB and may be placed on a wrist of a subject. In this case, the straps ST may be of a band type and may be integrally formed with or separated from each other. A laser irradiator 110 and a sensor 120 included in an apparatus 100 for acquiring bioinformation (of FIG. 3) may be arranged on an inner surface STb of the straps ST. In some exemplary embodiments, the sensor 120 may be one or more sensors arranged, for example, as a unit or an array.

When the bioinformation testing apparatus 10 is worn by a user, for example a subject P whose bioinformation is subject to be acquired, the laser irradiator 110 and the sensor 120 may be arranged to face a region of interest A of the subject P. In this case, the laser irradiator 110 and the sensor 120 may be located a distance from the region of interest A of the subject P and may acquire bioinformation of the subject P in a non-invasive manner.

The bioinformation of the subject P may include information about blood pressure, blood flow, etc. of the subject P. The blood pressure may mean pressure upon blood vessel walls when blood from the heart circulates in the blood vessels and may be classified into arterial pressure, capillary pressure, venous pressure, and the like according to names of the blood vessels. The arterial pressure varies with heart beats. Also, the blood pressure may include both systolic pressure, which is measured when blood flows in an artery during contraction of a ventricle, and diastolic pressure which is measured when blood does not flow in the artery during dilatation of the ventricle.

However, the subject P of the present disclosure is not limited to a person and may also be, for example, an animal. Also, the region of interest A of the subject P may include a region that moves, among body parts of a person or animal. For example, the region of interest A may include, but is not limited to, a neck, a chest, a wrist, legs, etc.

For example, when the bioinformation testing apparatus 10 is a wearable device of a watch type or a wrist-band type as illustrated in FIGS. 1 to 2B, the laser irradiator 110 and the sensor 120 may be arranged on the inner surface STb of the strap ST or an inner surface of the main body MB. Accordingly, when the subject P wears the bioinformation testing apparatus 10, the laser irradiator 110 and the sensor 120 may be arranged to face each other by a distance from the region of interest A of the subject P.

For example, when the subject P wears the bioinformation testing apparatus 10 on his or her wrist, the laser irradiator 110 irradiates a laser beam onto the region of interest A, and the laser beam emitted from the laser irradiator 110 is reflected from the region of interest A and may be detected by the sensor 120. In this case, the bioinformation testing apparatus 10 of the watch type or the wrist-band type may be used to measure blood pressure in the artery by irradiating, in a non-invasive manner, a laser beam onto the region of interest A, for example, a wrist, in more detail, a skin surface close to the radial artery. As illustrated in FIG. 2B, when blood pressure is measured on a skin surface of the wrist in which the radial artery lies, external factors causing errors, for example, a thickness of a skin tissue under the wrist, may affect the measurement of the blood pressure the least. Also, the radial artery is known as a blood vessel used to measure the blood pressure more accurately than other blood vessels. However, the present exemplary embodiment is not limited thereto. The bioinformation testing apparatus 10 may measure the blood pressure by using blood vessels in other parts of the wrist, other than the radial artery.

Also, the sensor 120 may acquire the bioinformation of the subject P by detecting, from the region of interest A, a change in a laser speckle pattern generated by the laser beam. For example, when a distribution of the laser speckles changes because the region of interest A where the laser beam is irradiated moves, an intensity of an optical signal corresponding to the laser speckles changes. In this case, the sensor 120 may detect an intensity change of the optical signal. The sensor 120 may acquire movement information of the region of interest A based on the intensity change of the optical signal (hereinafter, referred to as a change in the laser speckles) corresponding to the detected laser speckles and may acquire the bioinformation of the subject P based on the acquired movement information.

As described above, when the bioinformation of the subject P is acquired by using the bioinformation testing apparatus 10 in the non-invasive manner, a signal attenuation degree of the optical signal detected by the sensor 120 may differ according to an incident direction of a laser beam incident to the subject P and a reflection direction of a laser beam reflected from the subject P. For example, when the incident direction of the laser beam incident to the subject P is the same as the reflection direction of the laser beam, signal attenuation of an optical signal detected by the sensor 120 may occur due to a distance between the laser irradiator 110 and the sensor 120. Therefore, it may be necessary to adjust the incident direction, and when the incident direction is adjusted, the signal attenuation of the optical signal detected by the sensor 120 may be prevented. Hereinafter, an example of a detailed method of adjusting the incident direction of the laser beam incident to the subject P will be described, according to an exemplary embodiment.

Figure 3:
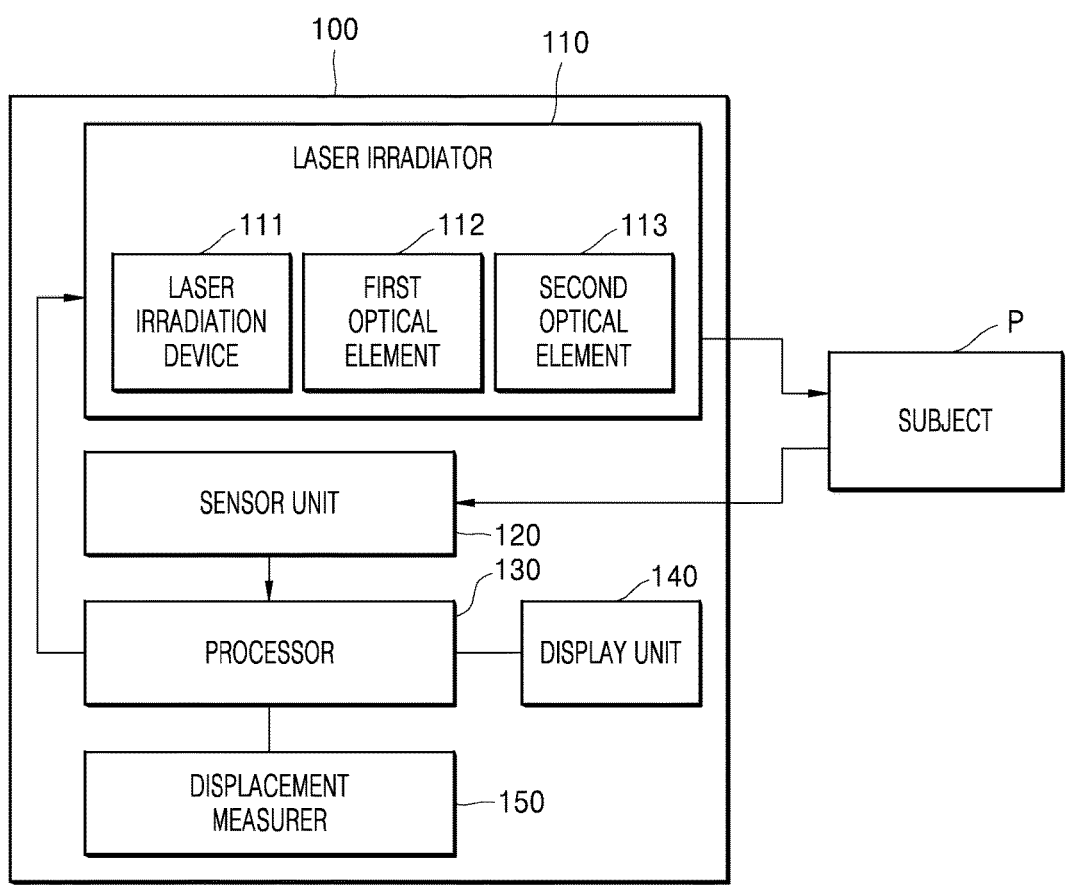
FIG. 3 illustrates a block diagram of a structure of an apparatus for acquiring bioinformation, according to an exemplary embodiment.

FIG. 3 illustrates a block diagram of a structure of an example of an apparatus 100 for acquiring bioinformation according to an exemplary embodiment.

Referring to FIG. 3, the apparatus 100 for acquiring bioinformation may include the laser irradiator 110, the sensor 120, a processor 130, a display 140, and a displacement measurer 150. The apparatus 100 for acquiring bioinformation may include more components than the components illustrated in FIG. 3.

The laser irradiator 110 irradiates a laser beam onto blood vessels (e.g., an radial artery) within the region of interest A (e.g., a wrist) of the subject P and may include a laser irradiation device 111, a first optical element 112, and a second optical element 113. For example, the laser irradiation device 111 may irradiate a laser beam and may include at least one laser diode device for oscillating the laser beam. Furthermore, the laser irradiation device 111 may further include a laser diode driver for controlling the laser oscillation, in addition to the laser diode device.

The first optical element 112 and the second optical element 113 are optical devices for adjusting an irradiation direction of the laser beam emitted from the laser irradiation device 111. For example, the first optical element 112 may be arranged on an optical path of the laser beam emitted from the laser irradiation device 111 and may refract, by a certain angle, the optical path of the laser beam that is incident to the first optical element 112. Thus, the irradiation direction of the laser beam emitted from the laser irradiation device 111 may be adjusted.

The second optical element 113 may be an optical device for adjusting an irradiation direction of a laser beam that is emitted from the laser irradiation device 111 or passes through the first optical element 112. For example, the second optical element 113 may be arranged on an optical path of a laser beam that passes through the first optical element 112 and may refract, by a certain angle, an optical path of a laser beam incident to the second optical element 113. Thus, an irradiation direction of the laser beam emitted from the laser irradiation device 111 may be adjusted.

A detailed description of an example of an adjustment of the irradiation direction by using the laser irradiation device 111 and the first and second optical elements 112 and 113 will be described below with reference to FIGS. 4A to 6B.

The sensor 120 detects, from the region of interest (e.g., a wrist), a change in a laser speckle pattern occurring due to scattering or interference of the irradiated laser beam. The laser speckles are irregular shapes (i.e., irregular patterns) generated due to the interference or scattering when a laser beam having coherency is irradiated onto a scatterer. The laser speckles may be in a form of scattered points on an image capturing the region of interest where the laser beam is irradiated.

The sensor 120 may include a dynamic vision sensor (DVS) and may detect an intensity change in optical signals corresponding to the laser speckles. The DVS may be a sensor for detecting an intensity change of light (an optical signal), and when the intensity of optical signals does not change, the DVS may enter a standby mode.

An image sensor for capturing image data, for example, a complementary metal-oxide semiconductor (CMOS) image sensor or a charged coupled device (CCD) image sensor, may present intensity (an amount) of optical signals in a form of analog information. On the contrary, the DVS may present, in a form of digital information, an indication of whether the intensity of optical signal changes, instead of the intensity of optical signals itself, (for example, an increase in intensity of light may be presented as +1, and no change in intensity of light may be presented as 0, and a decrease in the intensity of light may be presented as −1). Accordingly, the sensor 120 may detect the change in intensity of optical signals (hereinafter, referred to as a change in a laser speckle pattern) instead of the intensity of optical signals corresponding to the laser speckles.

When the region of interest where a laser beam is irradiated moves, a distribution pattern of the laser speckles may change, and the intensity of optical signals corresponding to the laser speckles may also change. Accordingly, when the region of interest moves, the sensor 120 may detect the change in the laser speckle pattern. For example, a blood flow amount within a blood vessel changes according to the contraction or relaxation of the heart, and according to a change of the blood flow amount, the blood vessel contracts or relaxes. Therefore, when the laser irradiator 110 irradiates a laser beam onto a region where the blood vessel lies, the distribution pattern of the laser speckles may change according to the contraction or relaxation of the blood vessel, and the sensor 120 may detect the change in the distribution pattern of the laser speckles.

The processor 130 may acquire a biosignal indicating a volume change according to the contraction or relaxation of the blood vessel (e.g., the radial artery) based on the change in the distribution pattern of the laser speckles and may predict blood pressure based on the acquired biosignal.

The processor 130 may acquire a biosignal based on a change in intensity of optical signals corresponding to laser speckles sensed by the sensor 120. For example, the processor 130 may acquire a biosignal by analyzing the laser speckle pattern changing according to the volume change of the blood vessel. The volume change of the blood vessel may correspond to a change in blood flow in a blood vessel, and thus, the biosignal acquired by analyzing the change in the laser speckle pattern may be a signal indicating the change in the blood flow. In some exemplary embodiments, the acquired biosignal may be a differential photoplethysmogram (PPG) signal.

The processor 130 may predict systolic pressure and diastolic pressure by using algorithms used to calculate pressure based on a signal indicating the change in the blood flow (e.g., a signal differentiating a PPG signal). For example, the processor 130 may extract at least one parameter from the acquired biosignal and may predict the systolic pressure and the diastolic pressure based on a correlation between the at least one extracted parameter and blood pressure.

Also, the processor 130 may generate a speckle change image based on the change in the laser speckle pattern detected by the sensor 120. The processor 130 may analyze a change in a temporal and spatial distribution pattern of laser speckles based on the change in intensity of optical signals corresponding to the laser speckles sensed by the sensor 120. Also, the processor 130 may analyze the temporal and spatial correlation regarding the region of interest by using the change in the distribution pattern of the laser speckles and may predict an accelerative change in blood flow. For example, the processor 130 may predict the accelerative change of the blood flow by using algorithms used to analyze the temporal and spatial correlation and the accelerative change in blood flow and may present the predicted accelerative change in blood flow in a two-dimensional (2D) image. Also, the processor 130 may acquire a velocity distribution of the blood flow based on the accelerative change in blood flow.

The display 140 may be a display device for displaying bioinformation of a user. For example, the display 140 may display information about blood pressure. In this case, the information about blood pressure may include numerical information regarding minimum blood pressure and maximum blood pressure of the user, numerical information regarding systolic pressure and diastolic pressure of the user, information of whether current blood pressure of the user is normal or abnormal, and the like. Also, the display 140 may display an image indicating an accelerative change in blood flow, an image indicating a velocity change in blood flow, or the like.

Also, for example, the display 140 may be embodied as a display panel, for example, a liquid crystal display (LCD) panel, and an organic light-emitting display (OLED) panel, arranged on the main body MB of the bioinformation testing apparatus 10 that is of a watch type as illustrated in FIG. 1.

The displacement measurer 150 may be a measurement device for measuring a distance between the laser irradiator 110 and the region of interest A of the subject P. For example, when the bioinformation testing apparatus 10 is of a watch type, the distance between the laser irradiator 110 and the region of interest A of the subject P, that is, the wrist, may change according to the movement of the subject P. The displacement measurer 150 may measure a change in the distance between the laser irradiator 110 and the region of interest A of the subject P according to the movement of the subject P. For example, the displacement measurer 150 may be embodied to measure the distance between the laser irradiator 110 and the region of interest A of the subject P by classifying a sensor device to which a laser beam is incident, from among the sensor 120, that is, sensor devices 121 to 125 as illustrated in FIG. 4B. However, the present disclosure is not limited thereto, and the displacement measurer 150 may be embodied to include an optical sensor on the same plane as the laser irradiator 110 and may measure the distance between the laser irradiator 110 and the region of interest A of the subject P.

Figure 4A:
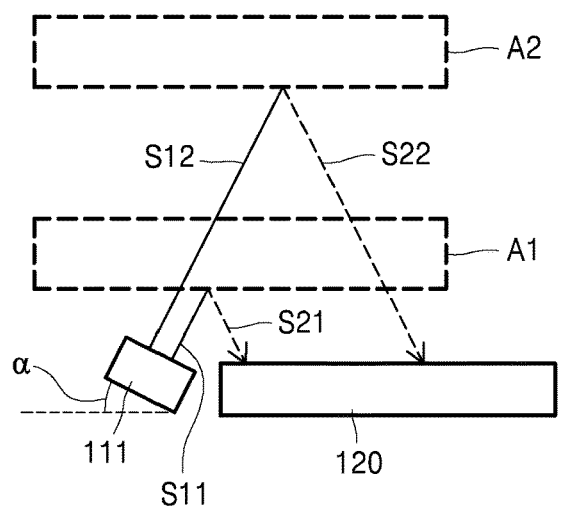
FIGS. 4A and 4B illustrate schematic diagrams of an apparatus for acquiring bioinformation, according to an exemplary embodiment.
Figure 4B:
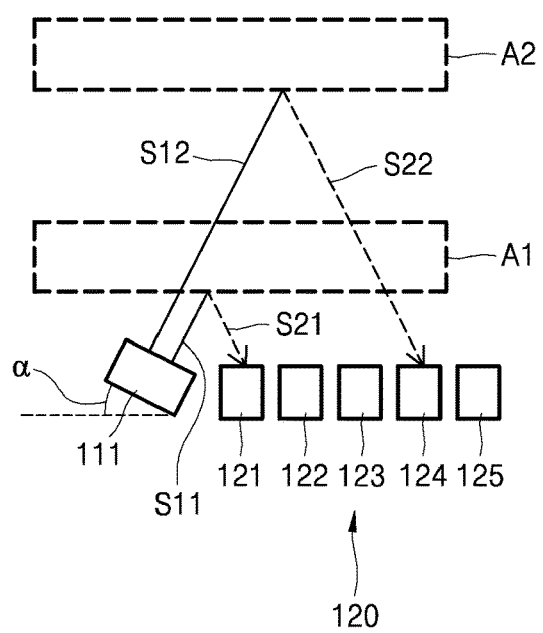

FIGS. 4A and 4B illustrate schematic diagrams of examples of an apparatus for acquiring bioinformation according to an exemplary embodiment.

Referring to FIGS. 4A and 4B, the laser irradiation device 111 and the sensor 120 are spaced apart from each other with an interval therebetween. In this case, the laser irradiation device 111 may be arranged to be tilted at a predetermined angle α, for example, at an angle that is equal to or greater than 30 degrees but less than or equal to 60 degrees, to the region of interest A of the subject P. In this case, the sensor 120 may extend in a direction as illustrated in FIG. 4A, or multiple sensor devices 121 to 125 of the sensor 120 may be spaced apart from each other at intervals in a direction as illustrated in FIG. 4B.

For example, when the sensor 120 extends in the direction as illustrated in FIG. 4A, a 1-1 laser beam S11 emitted from the laser irradiation device 111 is reflected from a first region of interest A1, and a 2-1 laser beam S21 reflected from the first region of interest A1 may be incident to a portion of the sensor 120. When a location of the region of interest A is moved from the first region of interest A1 to a second region of interest A2 as the subject P moves, a 1-2 laser beam S12 emitted from the laser irradiation device 111 is reflected from a portion of the second region of interest A2, and a 2-2 laser beam S22 reflected from the second region of interest A2 may be incident to another portion of the sensor 120.

Also, as another example, when the sensor 120 includes the sensor devices 121 to 125 as illustrated in FIG. 4B, the 1-1 laser beam S11 emitted from the laser irradiation device 111 is reflected from the first region of interest A1, and the 2-1 laser beam S21 reflected from the first region of interest A1 may be incident to the first sensor device 121. Also, when the location of the region of interest A is moved from the first region of interest A1 to the second region of interest A2 as the subject P moves, the 1-2 laser beam S12 emitted from the laser irradiation device 111 is reflected from the second region of interest A2, and the 2-2 laser beam S22 reflected from the second region of interest A2 may be incident to the fourth sensor device 124. In this case, as described with reference to FIG. 3, a distance between the region of interest A of the subject P and the laser irradiation device 111 may be measured in real time by checking a sensor device to which a laser beam is incident from among the sensor devices 121 to 125.

As described above, most laser beams emitted from the laser irradiation device 111 may be received by the sensor 120 by arranging the laser irradiation device 111 to be tilted at an angle α to the region of interest A. Accordingly, the signal attenuation according to the separation of the laser irradiation device 111 from the sensor 120 may be minimized, and an amount of power consumed to drive the laser irradiation device 111 may also be minimized.

Also, as the sensor 120 extends in the direction, the sensor 120 may receive a laser beam reflected from the first and second regions of interest A1 and A2 regardless of whether the region of interest A moves. Accordingly, the bioinformation testing apparatus 10 may acquire accurate bioinformation of the subject P during various wearing states where distances between the laser irradiation device 111 and the regions of interest A1 and A2 differ.

Figure 5A:
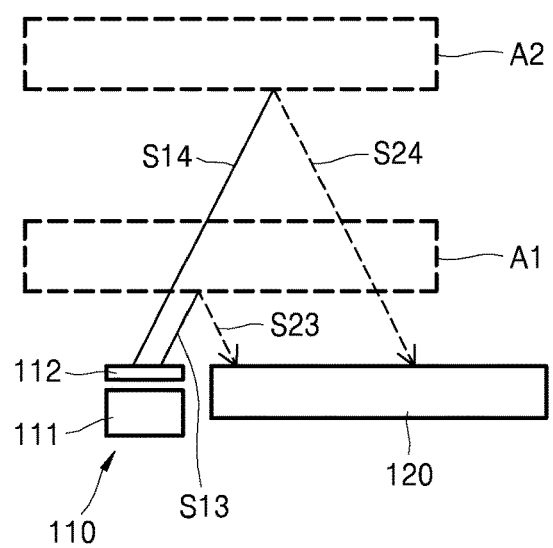
FIGS. 5A and 5B illustrate schematic diagrams of an apparatus for acquiring bioinformation, according to another exemplary embodiment.
Figure 5B:
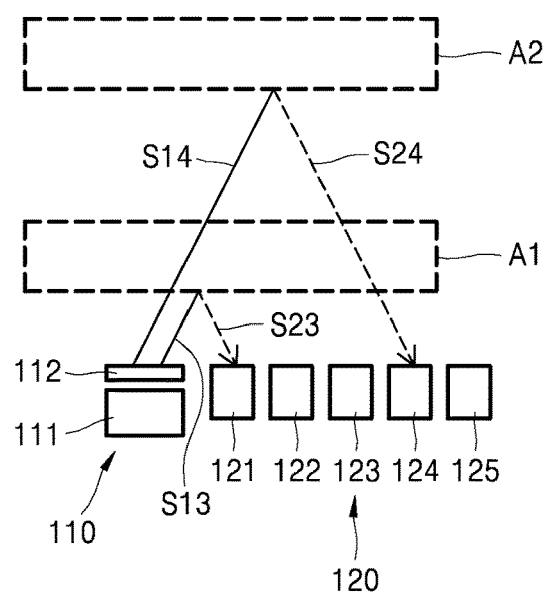

FIGS. 5A and 5B illustrate schematic diagrams of examples of the apparatus for acquiring bioinformation according to other exemplary embodiments.

In order to adjust an irradiation direction of the laser beam emitted from the laser irradiation device 111, the arrangement of the laser irradiation unit 111 may be adjusted, and an optical element may be used. Referring to FIGS. 5A and 5B, the laser irradiation device 111 and the sensor 120 may be spaced apart from each other with an interval therebetween. In some exemplary embodiments, the first optical element 112 may be arranged on an upper portion of the laser irradiation device 111, for example, an optical path of the laser beam emitted from the laser irradiation device 111, such that an irradiation direction of the laser beam may be adjusted.

For example, the first optical element 112 may include an optical lens having a meta material structure that may change the optical path of the laser beam emitted from the laser irradiation device 111. The meta material structure may be a structure in which fine pattern arrays are formed and is a device capable of focusing light on a certain location when light that is particularly patterned is incident to the meta material structure.

Figure 7A:
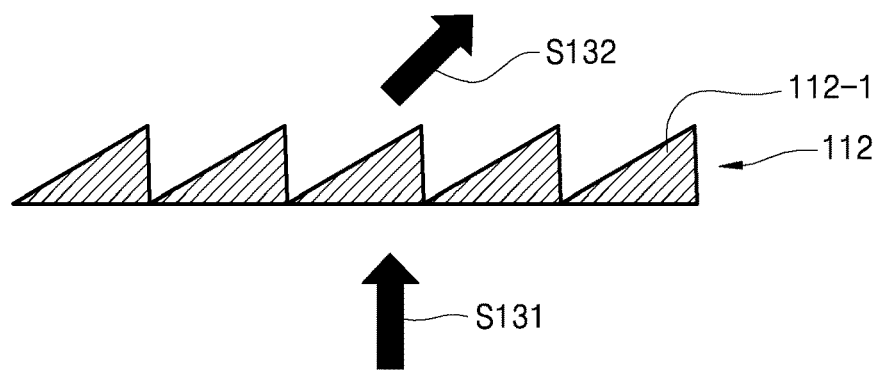
FIG. 7A illustrates a schematic diagram of a first optical element according to an exemplary embodiment.
Figure 8A:
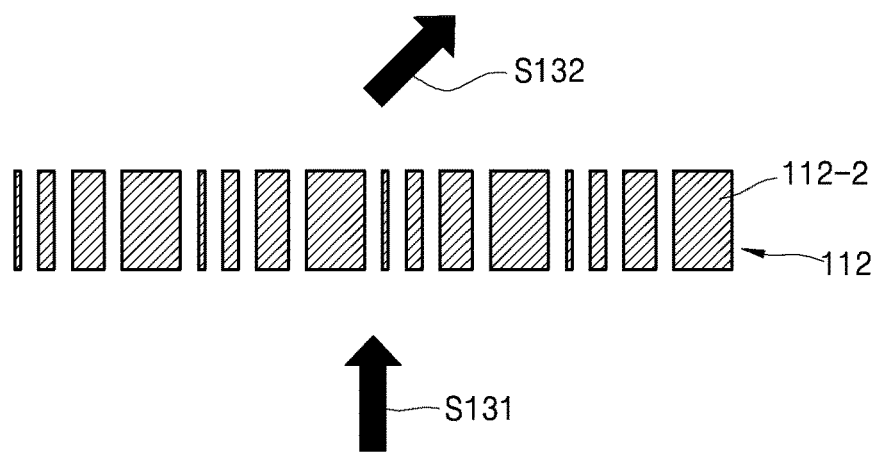
FIG. 8A illustrates a schematic diagram of a first optical element according to another exemplary embodiment.

For example, as illustrated in FIG. 7A or 8A, when the first optical element 112 includes a meta material structure of a grid pattern that includes first grids 112-1 or second grids 112-2, a first optical path S131 of a laser beam emitted from the laser irradiation device 111 may be changed to a second optical path S132 by the first optical element 112 having the meta material structure. The present disclosure discloses an optical lens having the meta material structure as the first optical element 112, but is not limited thereto.

Referring back to FIG. 5A, a 1-3 laser beam S13 whose optical path is changed by the first optical element 112 is reflected from the first region of interest A1, and a 2-3 laser beam S23 that is reflected from the first region of interest A1 may be incident to a portion of the sensor 120. When the location of the region of interest A is moved from the first region of interest A1 to the second region of interest A2 as the subject P moves, a 1-4 laser beam S14 whose optical path is changed by the first optical element 112 is reflected from the second region of interest A2, and a 2-4 laser beam S24 that is reflected from the second region of interest A2 may be incident to another portion of the sensor 120.

In some exemplary embodiments, when the sensor 120 includes the sensor devices 121 to 125 as illustrated in FIG. 5B, the 1-3 laser beam S13 whose optical path is changed by the first optical element 112 is reflected from the first region of interest A1, and the 2-3 laser beam S23 that is reflected may be incident to the first sensor device 121. Also, when the location of the region of interest A is moved from the first region of interest A1 to the second region of interest A2 as the subject P moves, the 1-4 laser beam S14 whose optical path is changed by the first optical element 112 is reflected from the second region of interest A2, and the 2-4 laser beam S24 that is reflected from the second region of interest A2 may be incident to the fourth sensor device 124.

As described above, most laser beams emitted from the laser irradiation device 111 may be received by the sensor 120 by arranging the first optical element 112 on the optical path of the laser beam. Accordingly, signal attenuation due to the separation of the laser irradiation device 111 from the sensor 120 may be minimized, and an amount of power consumed to drive the laser irradiation device 111 may be minimized.

Also, the sensor 120 may receive a laser beam reflected from the first and second regions of interest A1 and A2 regardless of whether the region of interest A moves, by extending the sensor 120 in a direction. Therefore, the bioinformation testing apparatus 10 may acquire accurate bioinformation of the subject P during various wearing states in which distances between the laser irradiation device 111 and the first and second regions of interest A1 and A2 differ.

Figure 6A:
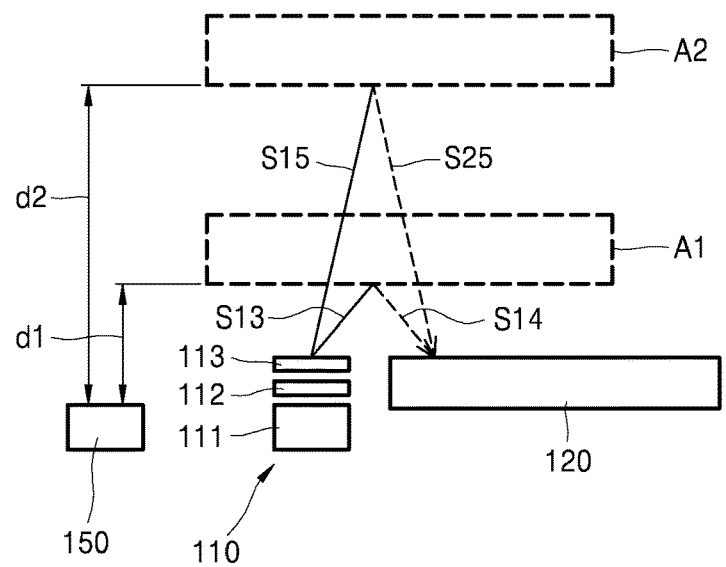
FIGS. 6A and 6B illustrate schematic diagrams of an apparatus for acquiring bioinformation, according to another exemplary embodiment.
Figure 6B:
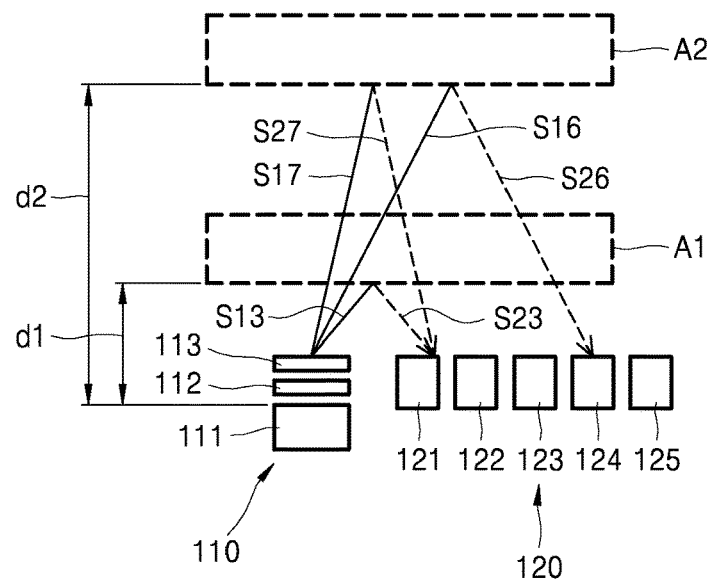

FIGS. 6A and 6B illustrate schematic diagrams of an apparatus for acquiring bioinformation according to other exemplary embodiments.

When an irradiation direction of a laser beam emitted from the laser irradiation device 111 is adjusted according to a distance between the region of interest A and the laser irradiation device 111, the bioinformation of the subject P may be acquired in various environments in which the bioinformation testing apparatus 10 is worn and the distance between the region of interest A and the laser irradiation device 111 may change. Referring to FIGS. 6A and 6B, the laser irradiation device 111 and the sensor 120 may be spaced apart from each other with an interval therebetween. In this case, the first optical element 112 and the second optical element 113 may be arranged on an upper portion of the laser irradiation device 111, for example, an optical path of the laser beam emitted from the laser irradiation device 111, and the irradiation direction of the laser beam may be adjusted according to the distance between the region of interest A and the laser irradiation device 111 by using the first optical element 112 and the second optical element 113.

Figure 7B:
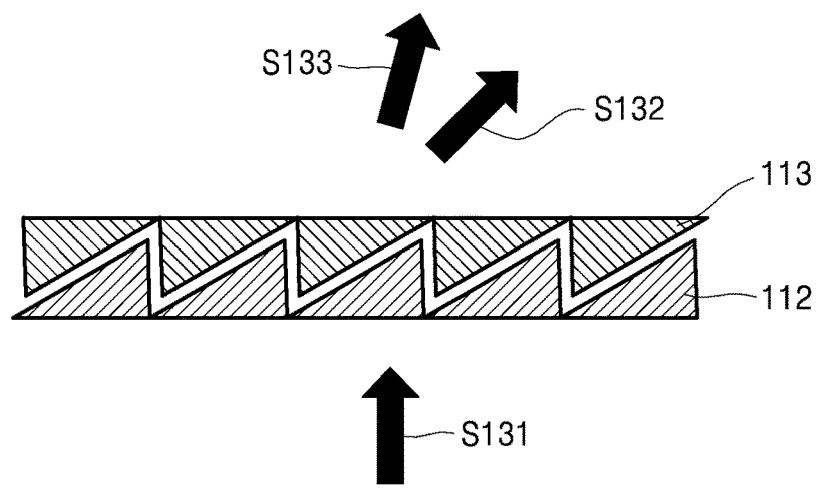
FIG. 7B illustrates a schematic diagram of the first optical element and a second optical element according to an exemplary embodiment.
Figure 8B:
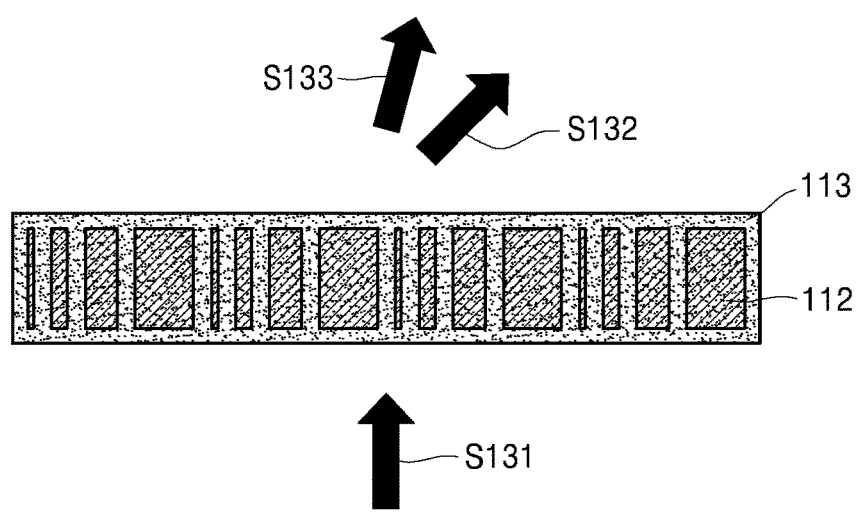
FIG. 8B illustrates a schematic diagram of the first optical element and a second optical element according to another exemplary embodiment.

For example, the second optical element 113 may be arranged on an upper portion of the first optical element 112 as illustrated in FIG. 7B or 8B and may include a material, for example, polymer network liquid crystals, having a refraction index that varies according to a property of electricity applied to the second optical element 113. For example, when the second optical element 113 includes polymer network liquid crystals, the processor 130 may control the property of electricity applied to the second optical element 113, and accordingly, the refraction index of the second optical element 113 may change in real time.

For example, the laser beam emitted from the laser irradiation device 111 is incident to the first optical element 112 and the second optical element 113, the first optical path S131 of the laser beam may be changed to the second optical path S132. In this case, when an electrical signal is transmitted to the second optical element 113 by the processor 130, the refraction index of the second optical element 113 may change. The first optical path S131 of the laser beam emitted from the laser irradiation device 111 may be changed to a third optical path S133.

Referring back to FIG. 6A, the 1-3 laser beam S13 that is emitted from the laser irradiation device 111 and passes through the first optical element 112 and the second optical element 113 is reflected from the first region of interest A1, and the 2-3 laser beam S23 that is reflected is incident to the sensor 120. In this case, the refraction index of the second optical element 113 may remain constant within a certain range.

When the location of the region of interest A is moved from the first region of interest A1 to the second region of interest A2 as the subject P moves, the displacement measurer 150 may measure changes in distances d1 and d2 between the laser irradiation device 111 and the first and second regions of interest A1 and A2. According to the changes in the distances d1 and d2 between the laser irradiation device 111 and the first and second regions of interest A1 and A2, the processor 130 may transmit an electrical signal to the second optical element 113, and thus, the refraction index of the second optical element 113 may change. As the refraction index of the second optical element 113 changes, a laser beam that is emitted from the laser irradiation device 111 and passes through the first optical element 112 and the second optical element 113 may be changed to a 1-5 laser beam S15. The 1-5 laser beam S15 whose optical path is changed is reflected from the second region of interest A2, and a 2-5 laser beam S25 that is reflected may be incident to the same portion of the sensor 120 as the portion where the 1-4 laser beam S14 is incident.

Referring back to FIG. 6B, the 1-3 laser beam S13 that is emitted from the laser irradiation device 111 and passes through the first optical element 112 and the second optical element 113 is reflected from the first region of interest A1, and the 2-3 laser beam S23 that is reflected is incident to the first sensor device 121. In this case, a refraction index of the second optical element 113 may remain constant within a certain range.

When the location of the region of interest A is moved from the first region of interest A1 to the second region of interest A2 as the subject P moves, a 1-6 laser beam S16 that is emitted from the laser irradiation device 111 and passes through the first optical element 112 and the second optical element 113 is reflected from the second region of interest A2, and a 2-6 laser beam S26 that is reflected may be incident to the fourth sensor device 124. In this case, the displacement measurer 150 may include the sensor devices 121 to 125 and may measure the changes of the distances d1 and d2 between the laser irradiation device 111 and the first and second regions of interest A1 and A2 by classifying a sensor device to which a laser beam is incident. As the distances d1 and d2 between the laser irradiation device 111 and the first and second regions of interest A1 and A2 change, the processor 130 may transmit an electrical signal to the second optical element 113, and accordingly, the refraction index of the second optical element 113 may change.

As the refraction index of the second optical element 113 changes, a 1-7 laser beam S17 that is emitted from the laser irradiation device 111 and passes through the first optical element 112 and the second optical element 113 is reflected from the second region of interest A2, and a 2-7 laser beam S27 that is reflected may be incident to the first sensor device 121 of the sensor 120.

As described above, a laser beam emitted from the laser irradiation device 111 may be incident to a certain portion of the sensor 120 regardless of the changes of the distances (d) between the laser irradiation device 111 and the first and second regions of interest A1 and A2 by controlling the refraction index of the second optical element 113. Accordingly, the bioinformation testing apparatus 10 may acquire accurate bioinformation of the subject P during various wearing states in which the distances between the laser irradiation device 111 and the first and second regions of interest A1 and A2 differ.

Figure 9:
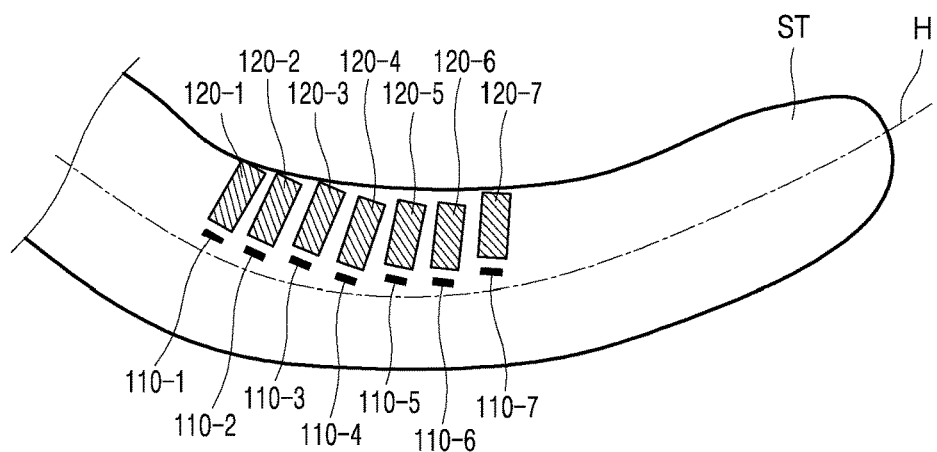
FIG. 9 illustrates a partial plan view of a bioinformation testing apparatus according to an exemplary embodiment.

FIG. 9 illustrates a plan view of the bioinformation testing apparatus 10 according to an exemplary embodiment.

As illustrated in FIGS. 2A and 2B, when the subject P wears the bioinformation testing apparatus 10 that is of a watch type or a wrist-band type, the bioinformation testing apparatus 10 may acquire accurate bioinformation when the laser irradiator 110 and the sensor 120 are arranged on the region of interest A, for example, the radial artery, in the same direction. According to a wearing state of the subject P, the laser irradiator 110 and the sensor 120 may not be arranged on the region of interest A, and thus, a separate operation of arranging the laser irradiator 110 and the sensor 120 may be necessary in order to acquire the accurate bioinformation. The apparatus 100 for acquiring bioinformation may be embodied in a multi-channel form having multiple laser irradiators 110 and the sensors 120 in order to avoid the necessity of the separate operation.

For example, referring to FIG. 9, laser irradiators 110-1 to 110-7 and sensors 120-1 to 120-7 may be spaced part from each other at intervals in a lengthwise direction of the straps ST. In this case, the laser irradiators 110-1 to 110-7 and sensors 120-1 to 120-7 may be arranged to respectively correspond to each other at intervals, and thus, the apparatus 100 for acquiring bioinformation may be arranged on the straps ST of the bioinformation testing apparatus 10.

Furthermore, when the bioinformation testing apparatus 10 is of a watch type or a wrist-band type, the laser irradiators 110-1 to 110-7 and the sensors 120-1 to 120-7 may be arranged in a direction, that is, a direction parallel to a forearm (refer to FIG. 2A), based on a central line H formed along the lengthwise direction of the straps ST in such a manner that the laser irradiators 110-1 to 110-7 and the sensors 120-1 to 120-7 may be arranged to face the radial artery of the subject P, that is, the region of interest A.

As described above, as the apparatus 100 for acquiring bioinformation is formed in a multi-channel form and is arranged on a certain location of the straps ST, for example, the direction parallel to the forearm, although a location of the bioinformation testing apparatus 10 on the region of interest A is changed due to the wearing state of the bioinformation testing apparatus 10 changing, the region of interest A of the subject P and the bioinformation testing apparatus 10 may be arranged with respect to each other. Accordingly, during various wearing states, since the region of interest A of the subject A and the bioinformation testing apparatus 10 may be arranged with respect to each other, bioinformation of the subject P may be accurately acquired without a separate arrangement process.

Figure 10:
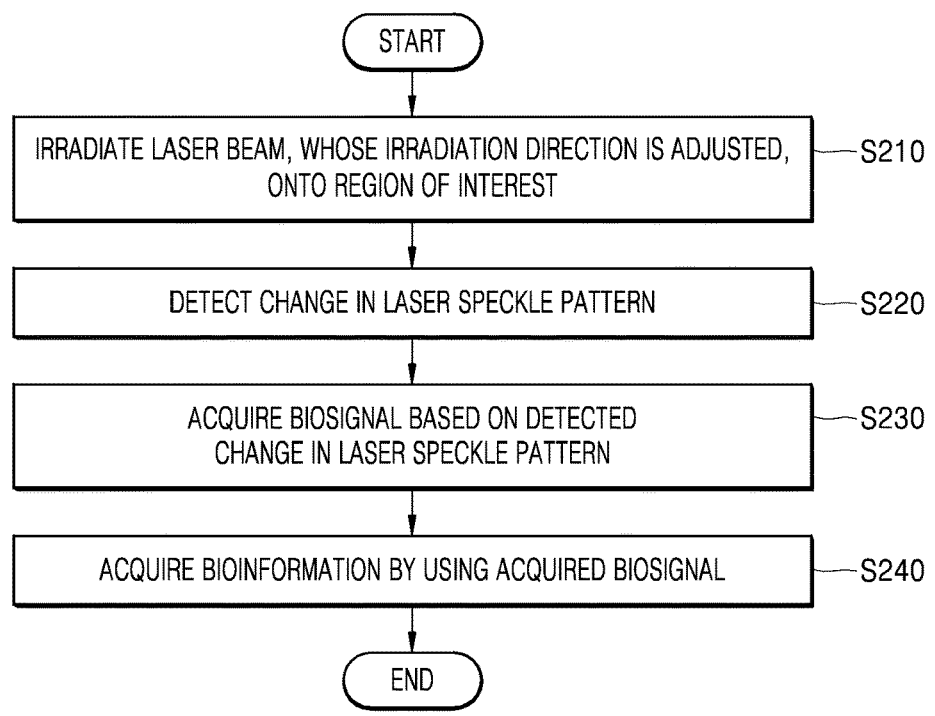
FIG. 10 illustrates a schematic flowchart of a method of acquiring bioinformation, according to an exemplary embodiment.

FIG. 10 illustrates a schematic flowchart of a method of acquiring bioinformation, according to an exemplary embodiment.

For example, in order to acquire the bioinformation, the subject P wears the bioinformation testing apparatus 10 of a watch type or a wrist-band type on a left or right wrist.

When a laser beam whose irradiation direction is adjusted is irradiated onto a region of interest including a blood vessel in operation S210, the irradiation direction of the laser beam is used to measure a change in a distance between the laser irradiation unit 110 and the region of interest A, and the irradiation direction of the laser beam may be adjusted according to the measured distance between the laser irradiation unit 110 and the region of interest A. Descriptions regarding the adjustment of the irradiation direction of the laser beam are substantially the same as the descriptions provided with reference to FIGS. 6A and 6B and thus are omitted.

In operation S220, a change in a laser speckle pattern is detected from the region of interest A.

When the laser irradiation unit 110 irradiates the laser beam onto the region of interest A, laser speckles may be generated due to an interference or scattering phenomena. In this case, due to movement (e.g., contraction and relaxation of the blood vessel according to a change in the amount of blood flow) of the blood vessel in the region of interest A, for example, the wrist, the laser speckles are changed. The sensor 120 receives the laser speckles reflected from the region of interest A and detects the change in the laser speckle pattern.

Then, the processor 130 may acquire a biosignal based on the change in the laser speckle pattern in operation S230 and may acquire the bioinformation by using the biosignal in operation S240.

For example, the processor 130 may acquire a biosignal indicating a volume change according to contraction and relaxation of a blood vessel (e.g., the radial artery) based on the change in the laser speckle pattern detected by the sensor 120 and may measure blood pressure based on the acquired biosignal. Also, the processor 130 may acquire a temporal and spatial correlation regarding the region of interest based on a change in distribution pattern of the detected laser speckles and may predict an accelerative change in blood flow based on the acquired temporal and spatial correlation.

In the apparatus and method of acquiring the bioinformation, an amount of power consumed to drive the laser irradiation device may be minimized by minimizing signal attenuation of the laser beam emitted from the laser irradiation device.

Also, the bioinformation may be acquired in various environments by adjusting the arrangement of the sensor and the irradiation direction of the laser beam.

In addition, the bioinformation of the subject may be accurately acquired during various wearing states by arranging the bioinformation testing apparatus and the subject in the same direction.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An apparatus for acquiring bioinformation, the apparatus comprising:
   a laser irradiator configured to irradiate a laser beam onto a region of interest including blood vessels;
   a sensor configured to detect a change in a laser speckle pattern generated by the laser beam reflected from the region of interest;
   a displacement measurer configured to determine a distance between the laser irradiator and the region of interest; and
   a processor configured to acquire a biosignal indicating a change in blood flow within the blood vessels based on the detected change in the laser speckle pattern, and to acquire the bioinformation based on the biosignal and the determined distance,
   wherein the laser beam emitted from the laser irradiator is incident at an angle to the region of interest,
   wherein an irradiation direction of the laser beam is adjusted according to the distance, and
   wherein the sensor comprises a plurality of sensor devices,
   wherein the plurality of sensor devices comprises a first sensor device spaced apart from a second sensor device, and
   wherein the displacement measurer is further configured to determine the distance to be a first distance in response to the laser beam being detected by the first sensor device, and to determine the distance to be a second distance in response to the laser beam being detected by the second sensor device.

2. The apparatus of claim 1, wherein the laser irradiator is arranged to be positioned at the angle with respect to the region of interest.

3. The apparatus of claim 1, further comprising a first optical element configured to adjust the irradiation direction of the laser beam.

4. The apparatus of claim 3,
   wherein the irradiation direction of the laser beam is adjusted according to the distance by modifying a refraction index associated with the laser irradiator, and
   wherein the refraction index comprises a refraction index of a second optical element configured to selectively adjust the irradiation direction of the laser beam.

5. The apparatus of claim 4, wherein the refraction index of the second optical element is determined based on the determined distance between the laser irradiator and the region of interest.

6. The apparatus of claim 3, wherein the first optical element comprises a meta material structure.

7. The apparatus of claim 1, wherein the plurality of sensor devices are spaced apart from each other at respective intervals in a direction with respect to the region of interest, and
   the laser irradiator comprises one or more laser irradiation devices that are arranged respectively corresponding to the plurality of sensor devices.

8. The apparatus of claim 1, wherein the plurality of sensor devices are spaced apart from each other at intervals in a direction with respect to the region of interest.

9. A bioinformation testing apparatus, the bioinformation testing apparatus comprising:
   a main body;
   straps connected to the main body; and
   an apparatus for acquiring bioinformation arranged on at least one from among an inner surface of the main body or an inner surface of the straps, wherein the apparatus for acquiring the bioinformation comprises:
   a laser irradiator configured to irradiate a laser beam onto a region of interest including blood vessels;
   a sensor configured to detect a change in a laser speckle pattern generated by the laser beam reflected from the region of interest;
   a displacement measurer configured to determine a distance between the laser irradiator and the region of interest; and
   a processor configured to acquire a biosignal indicating a change in blood flow within the blood vessels based on the detected change in the laser speckle pattern, and to acquire the bioinformation based on the biosignal and the determined distance,
   wherein the laser beam emitted from the laser irradiator is incident at an angle to the region of interest,
   wherein an irradiation direction of the laser beam is adjusted according to the distance, and
   wherein the sensor comprises a plurality of sensor devices, wherein the plurality of sensor devices comprises a first sensor device spaced apart from a second sensor device, and wherein the displacement measurer is further configured to determine the distance to be a first distance in response to the laser beam being detected by the first sensor device, and to determine the distance to be a second distance in response to the laser beam being detected by the second sensor device.

10. The bioinformation testing apparatus of claim 9, further comprising a plurality of sensors and laser irradiators, the plurality of sensors and laser irradiators being spaced apart from each other on an inner surface of the straps at intervals in a direction in which the straps extend.

11. The bioinformation testing apparatus of claim 10, wherein when a subject wears the bioinformation testing apparatus by using the straps, the apparatus for acquiring the bioinformation is arranged in a direction parallel to a forearm of the subject.

12. A method of acquiring bioinformation, the method comprising:

irradiating, using a laser irradiator, a laser beam onto a region of interest including blood vessels;

determining, using a displacement measurer, a distance between the laser irradiator and a skin surface corresponding to the region of interest;

detecting, using a sensor, a change in a laser speckle pattern from the region of interest;

acquiring, using a processor, a biosignal indicating a change in blood flow within the blood vessels using the detected change in the laser speckle pattern; and acquiring, using the processor, the bioinformation based on the biosignal and the determined distance, wherein an irradiation direction of the laser beam is adjusted according to the distance, wherein the sensor comprises a plurality of sensor devices, and wherein the plurality of sensor devices comprises a first sensor device spaced apart from a second sensor device, and wherein the determining further comprises determining the distance to be a first distance in response to the laser beam being detected by the first sensor device, and determining the distance to be a second distance in response to the laser beam being detected by the second sensor device.

* * * * *